United States Patent
Kent et al.

(10) Patent No.: US 10,004,900 B2
(45) Date of Patent: Jun. 26, 2018

(54) SYSTEMS AND METHODS FOR CORRELATING MEASUREMENTS IN NEUROSTIMULATION SYSTEMS

(71) Applicant: Pacesetter, Inc., Sunnyvale, CA (US)

(72) Inventors: Alexander Kent, Mountain View, CA (US); Gene Bornzin, Simi Valley, CA (US); Edward Karst, Los Angeles, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 184 days.

(21) Appl. No.: 14/527,668

(22) Filed: Oct. 29, 2014

(65) Prior Publication Data
US 2016/0121110 A1 May 5, 2016

(51) Int. Cl.
*A61N 1/36* (2006.01)
*A61B 5/00* (2006.01)
*A61B 5/11* (2006.01)
*A61N 1/05* (2006.01)

(52) U.S. Cl.
CPC ........ *A61N 1/36067* (2013.01); *A61B 5/1101* (2013.01); *A61B 5/7282* (2013.01); *A61N 1/36139* (2013.01); *A61N 1/0534* (2013.01)

(58) Field of Classification Search
CPC .. A61N 1/36; A61N 1/36067; A61N 1/36139; A61B 5/0476
USPC ...................................... 607/45, 62
See application file for complete search history.

(56) References Cited

U.S. PATENT DOCUMENTS

| | | | |
|---|---|---|---|
| 5,716,377 A | 2/1998 | Rise et al. | |
| 5,833,709 A | 11/1998 | Rise et al. | |
| 8,121,694 B2 | 2/2012 | Molnar et al. | |
| 2002/0177882 A1 | 11/2002 | DeLorenzo | |
| 2009/0099627 A1* | 4/2009 | Molnar | A61B 5/04014 607/62 |
| 2011/0112590 A1 | 5/2011 | Wu et al. | |
| 2012/0277820 A1* | 11/2012 | Wu | A61N 1/36067 607/45 |
| 2014/0213926 A1 | 7/2014 | Vaidyanathan | |

FOREIGN PATENT DOCUMENTS

| | | |
|---|---|---|
| EP | 0 895 483 B1 | 12/2003 |
| EP | 1 405 652 B1 | 2/2007 |
| WO | 2006/041738 A2 | 4/2006 |

\* cited by examiner

*Primary Examiner* — Carl H Layno
*Assistant Examiner* — Jon Eric C Morales
(74) *Attorney, Agent, or Firm* — Theresa A. Raymer

(57) ABSTRACT

The present disclosure provides systems and methods for correlating measurement in neurostimulation systems. A neurostimulation system includes a first sensor configured to acquire movement measurements for a subject, a second sensor configured to acquire neural measurements for the subject, and a computing device communicatively coupled to the first and second sensors. The computing device is configured to receive a movement signal from the first sensor, and receive a neural signal from the second sensor, wherein one of the movement signal and the neural signal is a trigger signal and the other of the movement signal and the neural signal is a signal of interest. The computing device is further configured to detect at least one trigger event in the trigger signal, and use the signal of interest based on the at least one trigger event.

20 Claims, 4 Drawing Sheets

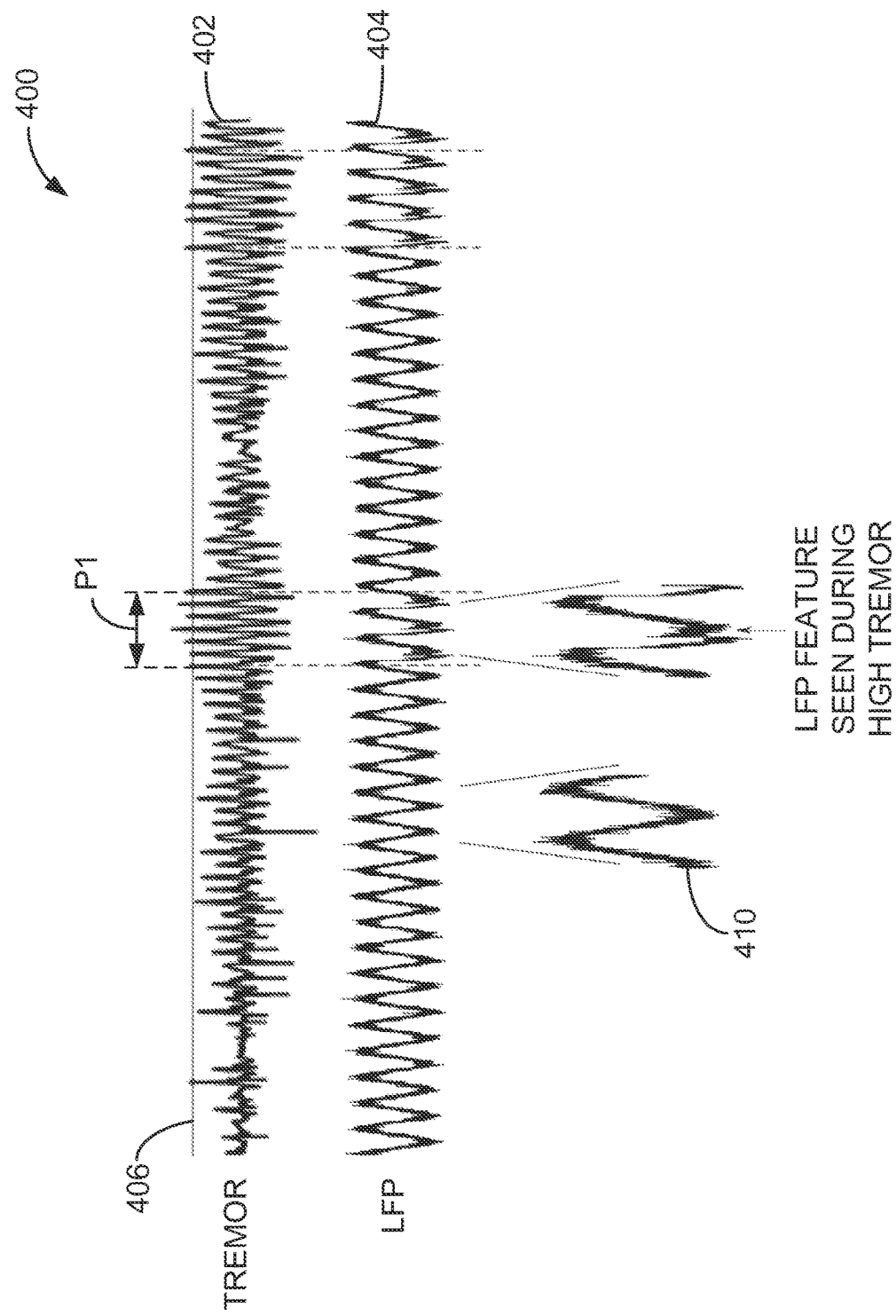

SYSTEMS AND METHODS FOR CORRELATING MEASUREMENTS IN NEUROSTIMULATION SYSTEMS

A. FIELD OF THE DISCLOSURE

The present disclosure relates generally to neurostimulation systems, and more particularly to correlating measurements between different types of sensors in neurostimulation systems.

B. BACKGROUND ART

At least some known closed-loop neuromodulation devices use biophysical signal feedback to perform automatic adjustment of stimulation parameters or titration of stimulation, which can facilitate maximizing therapeutic effectiveness, increasing power efficiency, and minimizing side effects. For example, for treatment of medically-refractory epilepsy, at least some known neuromodulation devices apply electrical stimulation in the brain only when epileptic neural activity is detected.

Several feedback signals have been proposed for closed-loop deep brain stimulation (DBS) devices that treat Parkinson's disease (PD), essential tremor (ET), or other movement disorders. One suitable signal is the local field potential (LFP), which represents synchronized neuronal oscillations within brain circuits and can be measured with a DBS lead. Pathological LFP activity may be correlated to motor symptoms, such as the known relationship between elevated beta band LFP oscillations (13-35 Hertz (Hz)) and bradykinesia/rigidity in PD. Another potential feedback signal is body motion measurement, which can indicate the presence or absence of tremor or other symptoms of PD or ET.

However, biophysical signals are generally noisy, making data analysis difficult in many cases. If a signal is periodic, one solution is to perform ensemble averaging to increase a signal-to-noise (SNR) ratio. This requires calculating the mean over time of individual signal responses, which increases SNR by the square root of the number of responses used in the average. However, there is a lack of external trigger events that can be used to align individual responses for ensemble averaging of LFP and/or tremor activity, since these are derived from spontaneous processes.

BRIEF SUMMARY OF THE DISCLOSURE

In one embodiment, the present disclosure is directed to a neurostimulation system. The neurostimulation system includes a first sensor configured to acquire movement measurements for a subject, a second sensor configured to acquire neural measurements for the subject, and a computing device communicatively coupled to the first and second sensors. The computing device is configured to receive a movement signal from the first sensor, and receive a neural signal from the second sensor, wherein one of the movement signal and the neural signal is a trigger signal and the other of the movement signal and the neural signal is a signal of interest. The computing device is further configured to detect at least one trigger event in the trigger signal, and use the signal of interest based on the at least one trigger event.

In another embodiment, the present disclosure is directed to a computing device for use with a neurostimulation system. The computing device includes a memory device, and a processing device communicatively coupled to the memory device. The processing device is configured to receive a movement signal from a first sensor configured to acquire movement measurements for a subject, receive a neural signal from a second sensor configured to acquire neural measurements for the subject, wherein one of the movement signal and the neural signal is a trigger signal and the other of the movement signal and the neural signal is a signal of interest, detect at least one trigger event in the trigger signal, and use the signal of interest based on the at least one trigger event.

In another embodiment, the present disclosure is directed to a method for correlating measurements in a neurostimulation system. The method includes receiving, at a computing device, a movement signal from a first sensor configured to acquire movement measurements for a subject, receiving, at the computing device, a neural signal from a second sensor configured to acquire neural measurements for the subject, wherein one of the movement signal and the neural signal is a trigger signal and the other of the movement signal and the neural signal is a signal of interest, detecting, using the computing device, at least one trigger event in the trigger signal, and using, using the computing device, the signal of interest based on the at least one trigger event.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 4 is a diagram illustrating correlations between a tremor signal and a local field potential signal.

Corresponding reference characters indicate corresponding parts throughout the several views of the drawings.

DETAILED DESCRIPTION OF THE DISCLOSURE

The present disclosure provides systems and methods for correlating measurement in neurostimulation systems. A neurostimulation system includes a first sensor configured to acquire movement measurements for a subject, a second sensor configured to acquire neural measurements for the subject, and a computing device communicatively coupled to the first and second sensors. The computing device is configured to receive a movement signal from the first sensor, and receive a neural signal from the second sensor, wherein one of the movement signal and the neural signal is a trigger signal and the other of the movement signal and the neural signal is a signal of interest. The computing device is further configured to detect at least one trigger event in the trigger signal, and use the signal of interest based on the at least one trigger event.

Neurostimulation systems are devices that generate electrical pulses and deliver the pulses to nerve tissue of a patient to treat a variety of disorders. One category of neurostimulation systems is deep brain stimulation (DBS). In DBS electrical pulses are delivered to parts of a subject's brain, for example, for the treatment of movement and effective disorders such as Parkinson's disease and essential tremor.

Neurostimulation systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. In DBS systems, the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted within a subcutaneous pocket created during the implantation procedure.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Figure 1:
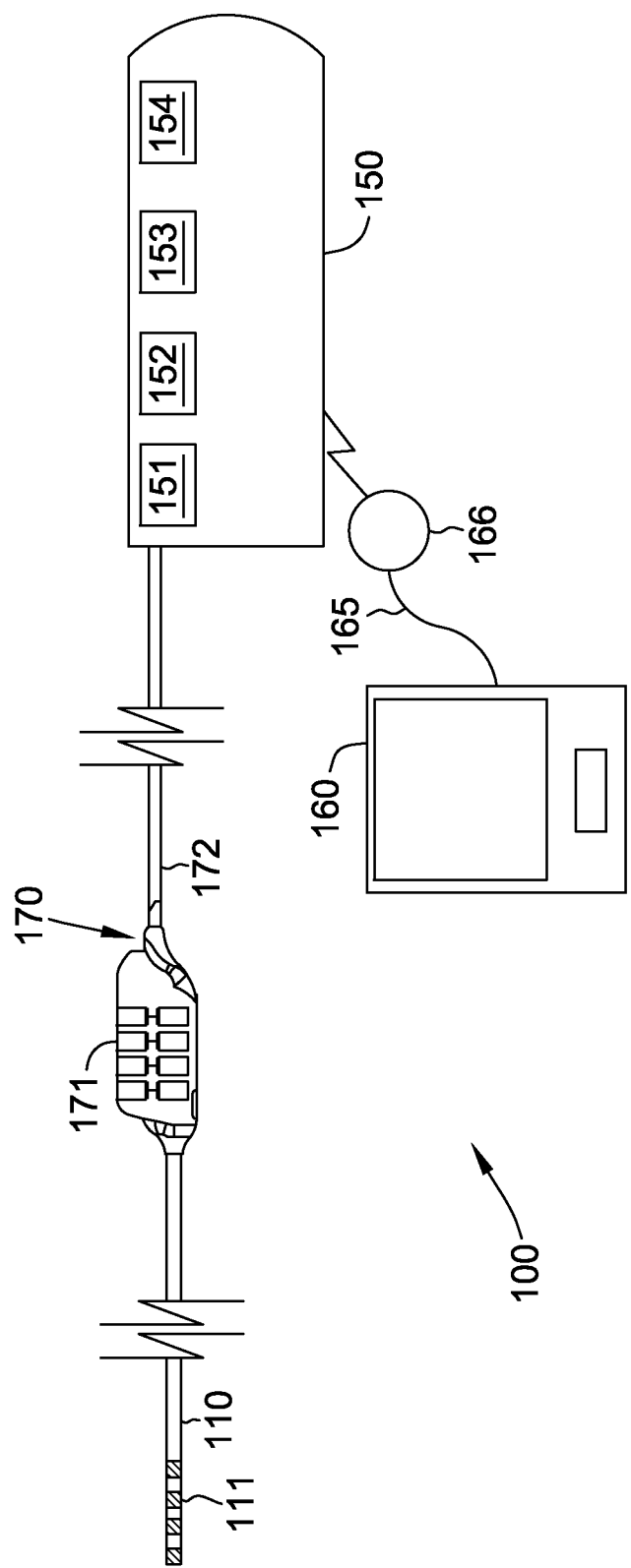
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of pulse generator 150 for execution by the microcontroller or processor to control the various components of the device.

Pulse generator 150 may comprise one or more attached extension components 170 or be connected to one or more separate extension components 170. Alternatively, one or more stimulation leads 110 may be connected directly to pulse generator 150. Within pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from pulse generator 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 2A:
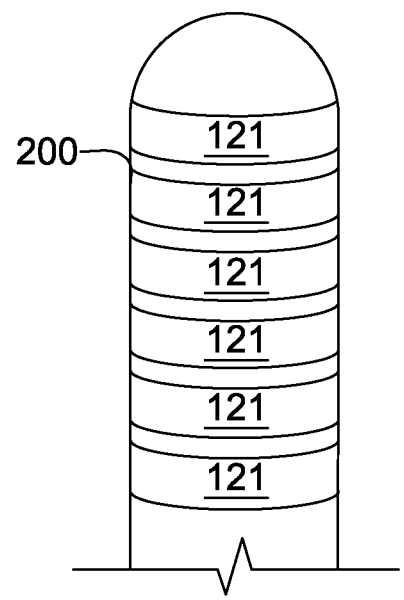
FIGS. 2A and 2B are schematic views of stimulation portions that may be used with stimulation system of FIG. 1.
Figure 2B:
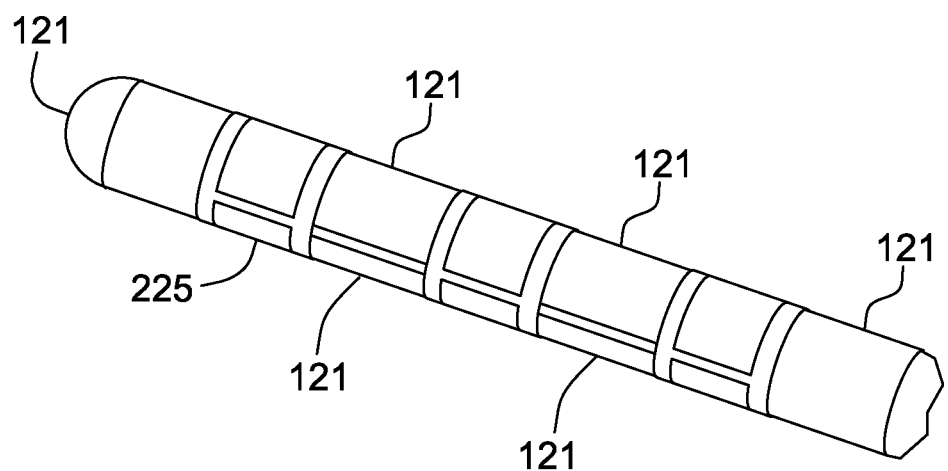

FIGS. 2A and 2B respectively depict stimulation portions 200 and 225 for inclusion at the distal end of lead 110. Stimulation portion 200 depicts a conventional stimulation portion of a lead including electrodes 121 that are ring electrodes. Stimulation portion 225 depicts a stimulation portion including several electrodes 121 that are segmented electrodes. The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference.

Returning to FIG. 1, controller device 160 may be implemented to recharge battery 153 of pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of generator 150. The charging circuitry may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 150 to be controlled by user after pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from St. Jude Medical, Inc. (Plano, Tex.).

Figure 3:
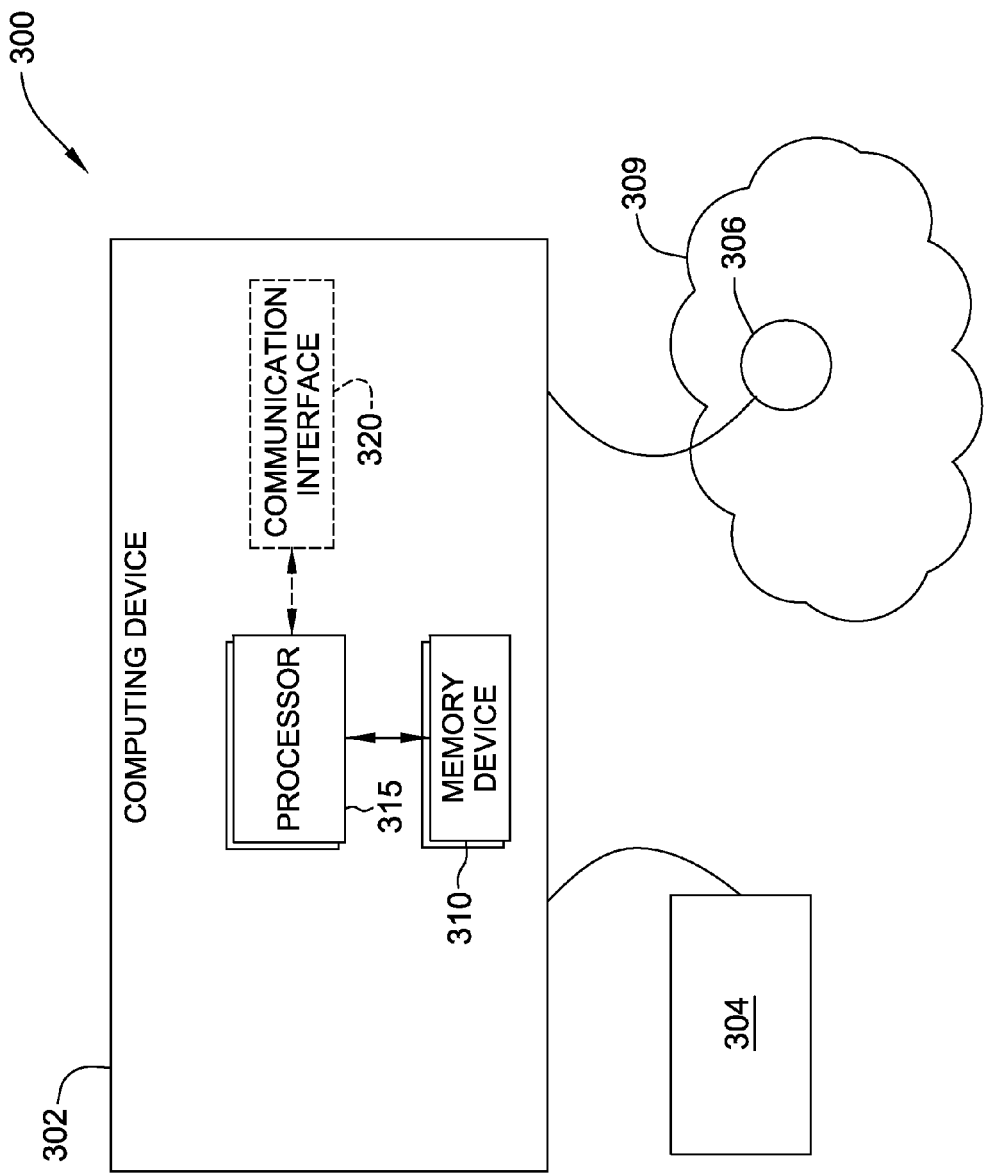
FIG. 3 is a schematic view of one embodiment of a neurostimulation system.

In FIG. 3, a neurostimulation system for deep brain stimulation (DBS) is indicated generally at 300. Neurostimulation system 300 includes a computing device 302 communicatively coupled to a first sensor 304 and a second sensor 306. Neurostimulation system 300 may be communicatively coupled to first and second sensors 304 and 306 using any suitable wireless and/or wired connection.

In this embodiment, first sensor 304 is a movement sensor, and second sensor 306 is an electrode sensor implanted in a brain 309 of the subject. Alternatively, first and second sensors 304 and 306 may be any type of sensing device that enables system 300 to function as described herein. Computing device 302 facilitates correlating measurements acquired by first and second sensors 304 and 306, as described herein.

Computing device 302 includes at least one memory device 310 and a processor 315 that is coupled to memory device 310 for executing instructions. In this embodiment, computing device 302 is implemented in an implantable pulse generator (IPG), such as IPG 150 (shown in FIG. 1). Executable instructions are stored in memory device 310. Computing device 302 performs one or more operations described herein by programming processor 315. For example, processor 315 may be programmed by encoding an operation as one or more executable instructions and by providing the executable instructions in memory device 310.

Processor 315 may include one or more processing units (e.g., in a multi-core configuration). Further, processor 315 may be implemented using one or more heterogeneous processor systems in which a main processor is present with secondary processors on a single chip. In another illustrative example, processor 315 may be a symmetric multi-processor system containing multiple processors of the same type. Further, processor 315 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. In the illustrated embodiment, processor 315 processes signals received from first and second sensors 304 and 306, as described herein. In the illustrated embodiment, processor 315 correlates measurements acquired by first and second sensors 304 and 306.

In the illustrated embodiment, memory device 310 is one or more devices that enable information such as executable instructions and/or other data to be stored and retrieved. Memory device 310 may include one or more computer readable media, such as, without limitation, dynamic random access memory (DRAM), static random access memory (SRAM), a solid state disk, and/or a hard disk. Memory device 310 may be configured to store, without limitation, application source code, application object code, source code portions of interest, object code portions of interest, configuration data, execution events and/or any other type of data.

Computing device 302, in the illustrated embodiment, includes a communication interface 320 coupled to processor 315. Communication interface 320 communicates with one or more remote devices, such as a clinician or patient programmer (not shown in FIG. 3). To communicate with remote devices, communication interface 320 may include, for example, a wired network adapter, a wireless network adapter, a radio-frequency (RF) adapter, a Bluetooth® adapter (Bluetooth is a registered trademark of Bluetooth SIG, Inc., a Delaware corporation), and/or a mobile telecommunications adapter.

In this embodiment, first sensor 304 acquires tremor measurements, and second sensor 306 acquires local field potential (LFP) measurements in brain 309. As will be appreciated by those of skill in the art, for subjects with Parkinson's disease (PD), essential tremor (ET), or other movement disorders (e.g., dyskinesia), there exists a causal relationship between tremor activity and LFP activity. In the systems and methods described herein, that causal relationship is utilized to improve measurement and signal analysis of tremor measurements and/or LFP measurements. More specifically, one of a tremor signal from first sensor 304 and an LFP signal from second sensor 306 is used as a trigger for recording and/or analysis of the other of the tremor signal and the LFP signal. For example, the coupling between tremor and LFP signals may be exploited to perform ensemble averaging and improve signal fidelity, as described herein. Moreover, use of two biophysical signals (e.g., tremor and LFP) in conjunction will more reliably represent the pathological state of a movement disorder than use of just one signal.

Although first sensor 304 acquires tremor measurements and second sensor 306 acquires LFP measurements in this embodiment, sensors 304 and 306 may acquire any type of signals that enables neurostimulation system 300 to function as described herein. For example, first sensor 304 may acquire movement signals related to tremors, bradykinesia, rigidity, gait problems, dyskinesia, and/or dysarthria. As used herein, "movement" refers to any physical body motion. Further, second sensor 306 may acquire neural signals related to LFPs, evoked potentials, and/or single-unit activity.

First sensor 304 is movement sensor for measuring tremor in one or more body areas. First sensor 304 may be an external or implanted sensor, and may include, for example, an accelerometer, a gyroscope, an inertial measurement unit, a goniometer, electromyogram electrodes (i.e., for measuring muscle motion), an optical sensor, and/or a video camera.

Locations for acquiring tremor measurements may include the head, chest, shoulder, upper arm, or lower arm of the subject. In one embodiment, first sensor 304 includes motion detectors (e.g., an accelerometer, gyroscope, or inertial measurement unit) or electromyogram electrodes placed externally and in wireless communication with an implantable pulse generator (IPG), such as IPG 150 (shown in FIG. 1). In another embodiment, first sensor 304 is implanted within the body, and is connected to the IPG via a wired or wireless connection. In yet another embodiment, first sensor 304 is included within the IPG, within a DBS electrode, or within a lead connecting the DBS electrode to the IPG. These locations facilitate acquiring and recording tremor measurements in the chest, head, and/or neck of the subject.

In embodiments where first sensor 304 includes electromyogram electrodes, the electromyogram electrodes may be placed on a surface of the IPG to record local myopotential activity in the chest. To shield the electromyogram electrodes from potentials generated by the heart, an isopotential may be set on the IPG surface to shunt such potentials, or the IPG may include a shielded exterior.

As indicated above, second sensor 306 is an electrode sensor implanted in brain 309. For example, second sensor 306 may measure LFP activity in the subthalamic nucleus or globus pallidus interna for Parkinson's disease. Further, for essential tremor and tremor-dominant Parkinson's disease, second sensor 306 may measure LFP activity in the ventral intermediate nucleus of the thalamus. Second sensor 306 may also measure activity at the surface (i.e., cortex) of brain 309. Second sensor 306 may utilize macro- or microelectrodes. For example, the LFP measurements may be acquired from macroelectrode contacts on the same DBS lead used for electrical stimulation, from contacts on a secondary DBS electrode used solely for recording, or from a recording microelectrode. Further, second sensor 306 may acquire measurements during the presence or absence of applied electrical stimulation.

In the illustrated embodiment, first sensor 304 transmits a tremor signal to computing device 302 that is indicative of tremor measurements acquired by first sensor 304. Similarly, second sensor 306 transmits a LFP signal to computing device 302 that is indicative of LFP measurements acquired by second sensor 306. Amplification and/or filtering may be applied to the tremor and LFP signals.

As described below, one of the tremor signal and the LFP signal is used as a trigger signal that triggers use of the other of the tremor signal and the LFP signal, referred to herein as the signal of interest. As used herein, "use" of a signal includes selecting, recording, processing, and/or any other use of the signal. This facilitates improving a signal-to-noise ratio of the signal of interest for subsequent post-processing or detection applications.

In one embodiment, the tremor signal is the trigger signal, and the LFP signal is the signal of interest. Specifically, the tremor signal is used as a trigger for alignment of individual responses and ensemble averaging of the LFP signal. For example, FIG. 4 is a diagram 400 showing a tremor signal 402 and an LFP signal 404 over a given time domain. Alternatively, a similar methodology may be performed in the frequency domain using periodogram averaging.

As shown in FIG. 4, variations in tremor signal 402 correspond to variations in LFP signal 404. For example, during a first period, P1, tremor signal 402 repeatedly rises above a predetermined threshold 406. During period P1, LFP signal 404 also includes anomalous features, as compared to a normal segment 410 of LFP signal 404. The magnitude of predetermined threshold 406 may be provided by a user (e.g., a physician) and/or stored, for example, on memory device 310.

The occurrence of tremor signal 402 exceeding predetermined threshold 406 is a detection event used for analyzing LFP signal 404. Specifically, computing device 302 compares tremor signal 402 to predetermined threshold 406, and processes LFP signal 404 based on one or more detection events. The detection events may be used to trigger recording of LFP signal 404 for a detection period and/or to align individual LFP cycles for ensemble averaging over multiple detection periods.

In one example, the detection period lasts a predetermined period of time (e.g., 1-10 seconds) after the first detection event. In another example, the detection period continues as long as a subsequent detection event occurs within a predetermined period of time (e.g., 1-10 seconds) from a most recent detection event (e.g., if the predetermined period of time is five seconds, the detection period will last until no further detection events occur for five seconds after the most recent detection event). In yet another example, the detection period lasts until the trigger signal falls back below the predetermined threshold.

Using this technique, periods of high and low tremor in LFP signal 404 can be differentiated from one another. Further, performing ensemble averaging of the LFP signal 404 over multiple detection periods facilitates improving the signal-to-noise (SNR) ratio of LFP signal 404, improving signal quality. The more detection periods used in the ensemble averaging, the more noise contamination will be filtered out of the signal.

Specifically, ensemble averaging increases the SNR by a factor of the square root of the number of detection periods used in the averaging. This is particularly useful in relatively sensitive data processing techniques that are strongly affected by noise, such as current source density analysis.

In another embodiment, the LFP signal is the trigger signal, and the tremor signal is the signal of interest. Similar to above, in this embodiment, computing device 302 determines detection events based on a comparison between the LFP signal and a predetermined threshold (either in the time domain or frequency domain), and uses the detection events to trigger recording of the tremor signal for a detection period and/or to align individual tremor events for ensemble averaging over multiple detection periods. The ensemble averaging facilitates detecting micro-tremors (i.e., relatively low amplitude tremors occurring in a body location different from the location of first sensor 304) that may be otherwise undetectable. For example, using the systems and methods described herein, an accelerometer coupled to an IPG in the chest of a subject may be able to detect a tremor originating in the arm of the subject.

The signal processing performed by computing device 302 may be used to administer stimulation to facilitate preventing or mitigating future tremors. For example, analysis of an ensemble averaged LFP signals may guide selection of contact configurations (e.g., on a segmented DBS lead) to facilitate maximal tremor reduction or reducing side effects (i.e., dyskinesias).

Further, the ensemble averaged tremor or LFP signal may be used for feedback in a closed-loop DBS system. That is, electrical stimulation parameters (e.g., frequency, amplitude, contact configurations, etc.) may be automatically (e.g., by computing device 302) adjusted based on the ensemble averaged signal. In some embodiments, electrical stimulation is only delivered when there is a relatively strong cross-correlation or coherence value between the tremor and LFP signals. Moreover, cross-correlation or coherence measurements between the tremor and LFP signals may be used to assess the relationship between the tremor and LFP signals at a range of frequency components.

The techniques described herein may also facilitate revealing distinct signal characteristics. For example, the LFP signal may have different characteristics during periods of high tremor than during periods of low tremor that are only ascertainable by performing triggered measurement and ensemble averaging, as described herein.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all ratter contained in the above description or shown in the accompanying drawings shall be interpreted as illustrative and not in a limiting sense.

What is claimed is:

1. A neurostimulation system comprising:
   a first sensor configured to acquire movement measurements for a subject;
   a second sensor configured to acquire neural measurements for the subject; and
   a computing device communicatively coupled to the first and second sensors, the computing device configured to:
   receive a movement signal from the first sensor related to tremors, bradykinesia, rigidity, gait problems, dyskinesia, and/or dysarthria;
   receive a neural signal from the second sensor related to local field potential (LFP), evoked potentials, and/or single-unit activity;
   utilize either the movement signal as a signal of interest and the neural signal as a trigger signal, or the neural signal as the signal of interest and the movement signal as the trigger signal;
   monitor for a trigger event in the trigger signal to thereby detect a plurality of the trigger events in the trigger signal over time;
   trigger recording of the signal of interest for a detection period, in response to each detection of the trigger event in the trigger signal, to thereby cause the signal of interest to be recorded for each of a plurality of detection periods;
   use the detections of the trigger event to align individual responses or cycles of the signal of interest over the plurality of detection periods;
   perform ensemble averaging of the aligned individual responses or cycles of the signal of interest to thereby produce an ensemble averaged signal of interest; and
   use the ensemble averaged signal of interest for at least one of administering stimulation by the neurstimulation system, or feedback in a closed-loop of the neurostimulation system.

2. The neurostimulation system of claim 1, wherein to detect at least one trigger event, the computing device is configured to detect when the trigger signal exceeds a predetermined threshold.

3. The neurostimulation system of claim 1, wherein to determine each detection period of the plurality of detection periods, the computing device is configured to determine the detection period as a predetermined period of time that begins at a respective one of the detections of the trigger event.

4. The neurostimulation system of claim 1, wherein to use the ensemble averaged signal of interest for at least one of administering stimulation by the neurstimulation system, or feedback in a closed-loop of the neurostimulation system, the computing device is configured to adjust stimulation parameters based on the ensemble averaged signal to facilitate optimizing therapy for the subject.

5. The neurostimulation system of claim 1, wherein the movement signal is the trigger signal and the neural signal is the signal of interest.

6. The neurostimulation system of claim 1, wherein the neural signal is the trigger signal and the movement signal is the signal of interest.

7. The neurostimulation system of claim 1, wherein the first sensor is configured to acquire tremor measurements for the subject, and wherein the second sensor is configured to acquire local field potential (LFP) measurements for the subject.

8. The neurostimulation system of claim 1, wherein each of the movement signal and the neural signal is one of a time-domain signal or a frequency-domain signal.

9. The neurostimulation system of claim 1, wherein the computing device is further configured to calculate a cross-correlation or coherence between the movement signal and the neural signal.

10. The neurostimulation system of claim 1, wherein the first sensor is configured to be positioned:
on an arm of the subject,
on a head of the subject,
within an implantable pulse generator (IPG),
on a surface of the IPG,
within a deep brain stimulation (DBS) electrode, and/or
within a lead connecting the DBS electrode to the IPG.

11. The neurostimulation system of claim 1, wherein the first sensor comprises electromyogram electrodes configured to be placed on a chest of the subject.

12. A computing device for use with a neurostimulation system, the computing device comprising:
a memory device; and
a processing device communicatively coupled to the memory device, the processing device configured to:
receive a movement signal related to tremors, bradykinesia, rigidity, gait problems, dyskinesia, and/or dysarthria from a first sensor configured to acquire movement measurements for a subject;
receive a neural signal related to local field potential (LFP), evoked potentials, and/or single-unit activity from a second sensor configured to acquire neural measurements for the subject;
utilize either the movement signal as a signal of interest and the neural signal as a trigger signal, or the neural signal as the signal of interest and the movement signal as the trigger signal;
monitor for a trigger event in the trigger signal to thereby detect a plurality of the trigger events in the trigger signal over time;
trigger recording of the signal of interest for a detection period, in response to each detection of the trigger event in the trigger signal, to thereby cause the signal of interest to be recorded for each of a plurality of detection periods;
use the detections of the trigger event to align individual responses or cycles of the signal of interest over the plurality of detection periods;
perform ensemble averaging of the aligned individual responses or cycles of the signal of interest to thereby produce an ensemble averaged signal of interest; and
use the ensemble averaged signal of interest for at least one of administering stimulation by the neurstimulation system, or feedback in a closed-loop of the neurostimulation system.

13. The computing device of claim 12, wherein to detect at least one trigger event, the processing device is configured to detect when the trigger signal exceeds a predetermined threshold.

14. The computing device of claim 12, wherein to determine each detection period of the plurality of detection periods, the computing device is configured to determine the detection period as a predetermined period of time that begins at a respective one of the detections of the trigger event.

15. The computing device of claim 12, wherein to detect at least one trigger event in the trigger signal, the processing device is configured to detect at least one trigger event in the movement signal.

16. A method for correlating measurements in a neurostimulation system, the method comprising:
receiving a movement signal from a first sensor configured to acquire movement measurements related to tremors, bradykinesia, rigidity, gait problems, dyskinesia, and/or dysarthria for a subject;
receiving a neural signal from a second sensor configured to acquire neural measurements related to local field potential (LFP), evoked potentials, and/or single-unit activity for the subject;
utilizing either the movement signal as a signal of interest and the neural signal as a trigger signal, or the neural signal as the signal of interest and the movement signal as the trigger signal;
monitoring for a trigger event in the trigger signal to thereby detect a plurality of the trigger events in the trigger signal over time;
triggering recording of the signal of interest for a detection period, in response to each detection of the trigger event in the trigger signal, to thereby cause the signal of interest to be recorded for each of a plurality of detection periods;
using the detections of the trigger event to align individual responses or cycles of the signal of interest over the plurality of detection periods;
ensemble averaging of the aligned individual responses or cycles of the signal of interest to thereby produce an ensemble averaged signal of interest; and
using the ensemble averaged signal of interest for at least one of administering stimulation by the neurstimulation system, or feedback in a closed-loop of the neurostimulation system.

17. The method of claim 16, wherein detecting at least one trigger event comprises detecting when the trigger signal exceeds a predetermined threshold.

18. The method of claim 17, wherein:
a LPF signal is the trigger signal,
a tremor signal is the signal of interest, and
detecting at least one trigger event comprises detecting when the LPF signal exceeds a predetermined threshold.

19. The method of claim 18, further comprising detecting micro-tremors using the ensemble average of the tremor signal.

20. The method of claim 16, wherein each recorded detection period of the plurality of detection periods comprises a portion of the signal of interest recorded for a predetermined period of time that begins at a respective one of the detections of the trigger event.

* * * * *